United States Patent [19]

Wieland

[11] 4,119,627

[45] Oct. 10, 1978

[54] PROCESS FOR THE MANUFACTURE OF 6β,7-METHYLENE-3-OXO-4-ENE STEROIDS

[75] Inventor: Peter Wieland, Oberwil, Switzerland

[73] Assignee: Ciba-Geigy Corporation, Ardsley, N.Y.

[21] Appl. No.: 782,585

[22] Filed: Mar. 29, 1977

[30] Foreign Application Priority Data

Apr. 6, 1976 [CH] Switzerland .................. 4299/76

[51] Int. Cl.$^2$ .............................................. C07J 71/00
[52] U.S. Cl. ..................... 260/239.57; 260/239.55 R; 260/397.4; 260/343.6; 260/347.8
[58] Field of Search .................. 260/239.55, 239.57

[56] References Cited

U.S. PATENT DOCUMENTS 3,531,503  9/1970  Cereghetti et al. ............. 260/397.3

*Primary Examiner*—Elbert L. Roberts
*Attorney, Agent, or Firm*—Theodor O. Groeger

[57] ABSTRACT

The invention provides a novel general process for the manufacture of 6β,7-methylene-3-oxo-4-ene-steroids by successively (a) reacting a 3ξ,5β-dihydroxy-6-ene-steroid which is optionally etherified or esterified in the 3-position with a zinc/copper-methylene iodide reagent to introduce the 6β,7-methylene bridge, (b) liberating an etherified or esterified 3-hydroxyl group if such a group is present, (c) treating the resultant 6β,7-methylene-3ξ,5β-dihydroxy-steroid with an oxidizing agent to dehydrogenate the 3-hydroxyl group to the oxo group, and (d) dehydrating the 6β,7-methylene-5β-hydroxy-3-oxo-steroid to form the 4,5-double bond. The starting materials, which form a novel class of compounds, can be obtained by a novel process by converting a 5β,6-oxido-3ξ-hydroxy-steroid with a selenol, for example phenylselenol, to a 6α-alkyl- or arylseleno-3ξ,5β-dihydroxy-steroid, oxidizing this compound with a peroxidic reagent, for example hydrogen peroxide, in a weakly acid medium to give the corresponding 6-selenonyl compound, and converting this compound, preferably by treatment with a base, preferably with 1,5-diazabicyclo[4,3,0]non-5-ene, to give the 3ξ,5β-dihydroxy-6-ene-steroid. During the course of these reactions, the 3-hydroxyl group is preferably temporarily protected by esterification or etherification.

20 Claims, No Drawings

PROCESS FOR THE MANUFACTURE OF 6β,7-METHYLENE-3-OXO-4-ENE STEROIDS

The invention relates to a novel process for the manufacture of 6β,7-methylene-3-oxo-4-ene steroids, especially of those of the general formula

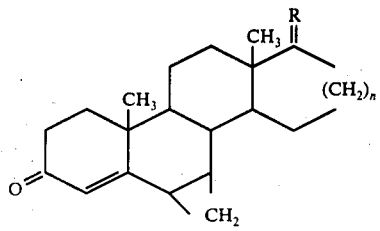

in which n denotes the number 1 or 2 and R represents an optionally ketalised oxo group, an optionally etherified or esterified hydroxyl group together with a hydrogen atom or an optionally substituted lower aliphatic hydrocarbon radical, or a hydrogen atom together with an optionally substituted lower alkyl radical.

Wherever it occurs in the context of an organic radical, the term "lower" denotes a corresponding radical with at most 7, and preferably with at most 4, carbon atoms.

The symbol n preferably denotes the number 1.

A lower alkyl radical is, for example, a n-propyl, i-propyl, n-butyl, i-butyl, sec.-butyl or tert.-butyl radical or a branched or, preferably, straight-chain pentyl, hexyl or heptyl radical, but above all an ethyl or methyl radical. A lower aliphatic hydrocarbon radical is to be understood meaning a lower alkyl radical, for example one of those already mentioned, which optionally also contains one or two multiple bonds, that is to say double bonds or triple bonds, such as, for example, a lower alkenyl, lower alkynyl and allenyl radical, for example a vinyl, allyl, methallyl, propargyl, hexadiynyl and, above all, ethynyl radical.

The lower aliphatic hydrocarbon radical or lower alkyl radical already characterised can be substituted by one or more substituents of the same type or of different types, these substituents being, above all, in the α-position and/or β-position (corresponding to the 20-position and 21-position respectively of steroid numbering). Potential substituents can be free or etherified and esterified hydroxyl groups, free or acetalised or ketalised oxo groups, for example, in an acetyl or hydroxyacetyl radical, and free or esterified carboxyl groups, it being possible for the carboxyl groups also to be in the form of their salts, especially alkali metal salts. An esterified carboxyl group is to be understood as meaning not only a carboxyl group which is in the form of its ester, especially in the form of an ester with lower alkanols, but also a carboxyl group which is bonded to a suitably distant hydroxyl group, which occurs as a substituent, to give a 6-membered or, in particular, a 5-membered lactone ring. A lactone ring of this type includes preferably the 17β-hydroxyl group and also analogous cyclic acetals and ethers (in which an acetalised formyl group or an etherified hydroxymethyl group, respectively, is present in place of the esterified carboxyl group) are included in the meaning of the optionally substituted hydrocarbon radicals discussed.

Accordingly, an especially preferred meaning of the said radical R is represented by the partial formula

in which $R^1$ represents two hydrogen atoms, an oxo group, or a lower alkoxy group together with a hydrogen atom.

The lower aliphatic hydrocarbon radical can also be substituted by a disubstituted amino group, for example a di-lower alkylamino group, such as the dimethylamino group or diethylamino group. A preferred meaning of R is a β-oriented hydroxyl group together with a γ-di-lower alkylaminopropyl radical, especially a γ-dimethylaminopropyl radical or γ-diethylaminopropyl radical.

A ketalised oxo group is derived, in particular, from lower alkanols, for example from methanol or ethanol, or preferably from α- or β-lower alkanediols, for example 1,2- or 1,3-propanediol, or, above all, ethylene glycol; however, it can also be derived from the corresponding sulphur analogues of the said alcohols and contain sulphur atoms in place of one or both oxygen atoms.

An etherified hydroxyl group can be a lower alkoxy group, especially a straight-chain lower alkoxy group, for example the methoxy, ethoxy, propoxy and butoxy group; however, it is above all a hydroxyl group etherified by an easily detachable protective group. The following are to be regarded, in particular, as the ether-like easily detachable protective groups: a lower alkyl radical substituted in the 1-position by aryl, especially phenyl, such as, for example, a benzyl radical and triphenylmethyl radical; a lower alkyl radical substituted in the 1-position by lower alkoxy groups, such as those mentioned above, for example the 1-butoxyethyl radical or 1-methoxyethyl radical; and also heterocyclic radicals of the 2-tetrahydrofuryl and, in particular, 2-tetrahydropyranyl radical type; and finally also a silyl group which is trisubstituted by identical or different hydrocarbon radicals, especially a trilower alkylsilyl group, for example the trimethylsilyl group and dimethyl-tert.-butylsilyl group. The 17α,20;20,21-bis-methylenedioxy grouping may also be mentioned as a special case of etherified hydroxyl groups.

An esterified hydroxyl group is, in particular, a hydroxyl group which is esterified by a carboxylic acid; however, as stated above, it can also be a lactonised hydroxyl group.

Acids which can be used as the carboxylic acid component of an esterified hydroxyl group are, above all, the carboxylic acids customary in steroid chemistry, for example monocarboxylic acids with at most 18 carbon atoms, such as aliphatic carboxylic acids, especially formic acid or a lower alkanecarboxylic acid in which the lower alkyl radical is one of those mentioned above, above all propionic acid, butyric acid, isobutyric acid, valeric acid, isovaleric acid, oenanthic acid and diethylacetic acid, and above all caproic acid, trimethylacetic acid and acetic acid; but also corresponding halogenated lower alkanecarboxylic acids, such as chloroacetic acid, trichloroacetic acid or trifluoroacetic acid; as well as cycloaliphatic, cycloaliphatic-aliphatic and aromatic carboxylic acids, for example benzoic acids which are optionally substituted by halogen, such as fluorine, chlorine or bromine, hydroxyl, lower alkoxy, lower alkyl and/or nitro, or corresponding aryl- or aryloxy-lower alkanecarboxylic acids, but also corresponding dicarboxylic acids with at most 12 carbon atoms, for example succinic acid, glutaric acid, adipic acid and phthalic acid.

The 6β,7-methylene-3-oxo-4-ene steroids which can be manufactured according to the invention can be used as intermediates for the synthesis of valuable pharmaceutical active compounds and especially of those used for hormone therapy and/or as an additive in feedstuffs. Some of the compounds, for example those singled out in particular further below, at the same time themselves show a biological activity and, accordingly, can be used directly as active compounds in the above mentioned fields of application.

Steroid compounds containing the 6β,7-methylene-3-oxo-4-ene grouping have hitherto been manufactured by addition of the methylene group to the 6,7-double bond of a corresponding 3-oxo-4,6-diene using dimethyloxosulphonium methylide as reagent. However, the addition reaction in no way proceeds in a stereospecific manner and always gives mixtures of the 6α,7-epimer and 6β,7-epimer, in which the α-epimer usually predominates to a greater or lesser extent, compare, for example, N. H. Dyson, J. A. Edwards and J. H. Fried: Tetrahedron Letters, 1966, 1841–1844. This lack of stereospecificity has also been observed when the analogous dichloromethylene or difluoromethylene group is introduced by addition of dichloro- or difluorocarbene onto the 6,7-double bond, compare, for example, C. Beard, B. Berkoz et al., Tetrahedron 1969, 25, 1219. Because physical properties of the resulting epimers differ only very slightly, they can be separated only with difficulty, with considerable loss and often only incompletely. The methods of separation used for this purpose, for example thin-layer chromatography, repeated fractional crystallisation and the like, are completely unsuitable for industrial manufacture because of the complexity involved. Therefore, the solution to the problem was primarily to be sought in as stereospecific as possible a synthesis for this grouping.

As has now been found, the addition of the methylene group to the 6,7-double bond surprisingly proceeds in an extremely stereospecific manner and virtually with the exclusive formation of the 6β,7-methylene epimer, by reacting a steroid compound which contains the 6-en-3ξ,5β-diol grouping, or an 3-ether or 3-ester thereof, with a zinc/copper-methylene iodide reagent. The 3-hydroxyl group in the 6β,7-methylene-3ξ, 5β-dihydroxy grouping thus formed can, after a preceding liberation from the etherified or esterified form if necessary, be dehydrogenated with conventional oxidising agents and the resulting 6β,7-methylene-5β-hydroxy-3-oxo grouping can be dehydrated surprisingly smoothly under mild conditions to give the desired 6β,7-methylene-3-oxo-4-ene grouping. These 3 or 4 reaction stages (addition of the methylene group, liberation, if necessary, of the hydroxyl group, dehydrogenation and dehydration) need not be carried out consecutively in an uninterrupted sequence, but it is possible, if desired, to carry out appropriate additional steps, for example for converting a substituent in the 17-position, between the individual stages according to the invention.

The process according to the invention is preferably carried out in such a manner that, successively, a compound of the formula III

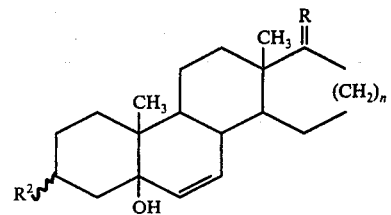

in which $n$ and R have the above general and preferred meanings and $R^2$ represents an α-oriented or, in particular, β-oriented hydroxyl group which can be etherified by an easily detachable protective group or can be esterified by a carboxylic acid, (a) is reacted with a zinc/copper-methylene iodide reagent, (b) an 3-ether or 3-ester, if present, is converted into a corresponding 3-hydroxy compound, (c) the corresponding 6β,7-methylene-3ξ,5β-diol is treated with an oxidising agent in order to dehydrogenate the 3-hydroxyl group and (d) the resulting 6β,7-methylene-5β-hydroxy-3-oxo compound is dehydrated. If desired, further optional reactions for interconversion of the group R within the scope of the meaning indicated above can be inserted between the reaction stages (a)–(d).

The metal-organic reagent for reaction stage (a) according to the invention, that is to say the zinc/copper-methylene iodide reagent, is prepared in situ by allowing methylene iodide (diiodomethane, $CH_2I_2$) to act on finely divided zinc/copper alloy. The zinc/copper alloy mentioned is obtained by treating finely divided zinc, preferably in the form of zinc dust, with a copper salt, especially a copper (II) salt, such as copper sulphate. The preparation of the zinc/copper alloy is usually carried out in an aqueous medium; at the end of the preparation, the water is decanted off and replaced by a suitable organic solvent by repeated decanting. The instructions given by E. Le Goff: J. Org. Chem. 1964, 29, 2048 can serve as an example of an advantageous variant of the preparation of the alloy. The reaction of the zinc/copper alloy with methyl iodide is carried out with the exclusion of water and alcohols in a saturated open-chain or cyclic ether or polyether, or a mixture of two or more of these solvents, at temperatures which extend from about 10° C. up to the boiling point of the reaction mixture. If desired, the reaction can be initiated by activating with a small amount of iodine. Among the ethers and polyethers already mentioned, symmetrical di-lower alkyl ethers, such as diethyl ether or diisopropyl ether, and polyethers derived from glycols, such as ethylene glycol dimethyl ether or ethylene glycol diethyl ether and diethylene glycol dimethyl ether and also tetrahydrofurane, tetrahydropyrane and dioxane are preferred in particular. Tetrahydrofurane and, above all, diethyl ether, and primarily ethylene glycol dimethyl ether (1,2-dimethoxyethane), are particularly advantageous. Other aprotic solvents or diluents, such as, for example, aliphatic or aromatic inert hydrocarbons, such as hexane, cyclohexane, benzene or toluene, can be mixed with these ethers.

The reaction of the steroid with the reagent is usually carried out directly after the reagent has been prepared, by adding the steroid compound which is to be reacted, preferably as a solution in one of the solvents mentioned. The reaction is usually carried out at elevated temperature, preferably under atmospheric pressure at the boiling point of the reaction mixture. It is also possible to work at constant volume by distilling off the solvent during the addition of the steroid, or to carry out the reaction with the nascent organo-metallic reagent by adding the steroid to be reacted and methylene iodide simultaneously, in portions, to an excess of the zinc/copper alloy and a small amount of the prepared organo-metallic reagent in the said medium. The reaction is usually carried out under atmospheric pressure, but it is also possible to work under elevated pressure. After the reaction is complete, the reaction mixture is worked up by hydrolysis; the conditions for the hydrolytic work-up are those which are customarily used for this purpose in the chemistry of organo-metallic compounds, and especially of organo-zinc compounds. The procedure according to H. E. Simmons et al., J. Am. Chem. Soc. 1958, 80, 5323 and 1964, 86, 1347 may be mentioned as an example of the reaction described above, including the preparation of the organo-metallic reagent and the working up.

It will be understood that the liberation of the 3-hydroxyl group mentioned under process stage (b) according to the invention is carried out only if starting materials of the formula III are used in which $R^2$ denotes a hydroxyl group which is protected by esterification or etherification in the manner indicated above under formula III; if $R^2$ is a free hydroxyl group, this reaction stage is, of course, omitted. The liberation according to stage (b) is carried out in a manner which is in itself known, preferably by hydrolysis. The hydroxyl groups etherified by easily detachable protective groups (including the silyloxy groups) are preferably hydrolysed under acid catalysis, and in each case conditions which are as mild as possible are to be recommended. The hydrolysis is carried out in the presence of an inorganic acid, for example sulphuric acid or a hydrogen halide acid, such as hydrochloric acid, hydrobromic acid or hydriodic acid, or of an organic sulphonic acid, such as p-toluenesulphonic acid or sulphosalicylic acid, or, preferably, of a carboxylic acid of medium strength, such as oxalic acid, acetic acid or formic acid. The hydroxyl group can also be liberated from a benzyloxy group or triphenylmethoxy group by hydrogenolysis, for example by hydrogenation on a palladium catalyst. The hydroxyl groups esterified by carboxylic acids can also be hydrolysed under acid conditions; however, they are preferably hydrolysed under base catalysis. The basic catalysts used are preferably hydroxides, carbonates or bicarbonates of the alkali metals, and especially of sodium or potassium. Esterified hydroxyl groups can also be liberated by reduction, for example by the action of an ester-reducing agent, such as of a complex hydride or diborane. In compounds which, in addition to the said etherified or esterified 3-hydroxyl group, also possess hydroxyl groups of the same type in the 17-position and/or 21-position, the latter are usually also liberated at the same time as the former.

The dehydrogenation of the 3-hydroxyl group to the 3-oxo group according to reaction stage (c) is also carried out in a manner which is in itself known. Preferred oxidising agents for this reaction are compounds of hexavalent chromium, such as chromium trioxide and chromic acid and alkali metal salts of the latter. Lower alkanecarboxylic acids, such as acetic acid or propionic acid, or pyridine or, in particular, acetone, optionally in combination with a halogenated lower alkane, such as dichloromethane or chloroform, and/or in the presence of aqueous sulphuric acid, are advantageously used as the reaction medium. Another alternative for the oxidation of the hydroxyl group is the Oppenauer oxidation, that is to say the oxidation with a ketone, such as acetone or cyclohexanone, under the catalytic influence of an aluminium lower alkoxide, such as aluminium isopropylate; under certain circumstances, a spontaneous dehydration according to reaction stage (d) takes place, at least in part, under the conditions of the oxidation or of the work-up of the reaction mixture.

The dehydration indicated under reaction stage (d) according to the invention is also carried out in a manner which is in itself known by eliminating the elements of water. The elimination of water can be catalysed by bases, and in particular by acids; a particularly advantageous procedure consists in heating the corresponding $6\beta,7$-methylene-$5\beta$-hydroxy-3-oxo compound in acetic acid. In the last-mentioned case, this treatment is preferably carried out after the preceding dehydrogenation, without purification of the intermediate.

The reactions which optionally can be carried out and which, if desired, can be inserted between reaction stages (a)–(d) according to the invention include, in particular, the following conventional conversions of steroid chemistry: acid-catalysed hydrolysis of a ketalised 17-oxo group; conversion of the 17-oxo group into the $17\beta$-hydroxyl group, optionally with simultaneous introduction of an optionally substituted lower aliphatic hydrocarbon radical; hydrogenation of an acetylenic hydrocarbon radical; esterification or etherification of a hydroxyl group; and closure of a lactone ring in a hydroxycarboxylic acid. The first three conversions are advantageously effected after stage (a) according to the invention and the penultimate conversion is preferably carried out, especially in the case of tertiary hydroxyl groups, following-on process stage (c). In certain circumstances, closure of the lactone ring can take place spontaneously simultaneously with process stage (d), especially on warming in acetic acid.

The optional acid-catalysed hydrolysis of the ketalised 17-oxo group is carried out in a manner which is in itself known, advantageously under conditions analogous to those indicated above for the hydrolysis of ether-like easily detachable protective groups.

The optional conversion of the 17-oxo group into a $17\beta$-hydroxyl group is above all carried out by reduction. The reduction is carried out in a manner which is in itself known; advantageously, diborane or complex hydrides, especially those of aluminium or boron with an alkali metal or alkaline earth metal, such as, for example, sodium aluminium hydride, calcium borohydride or lithium borohydride, but especially lithium aluminium hydride and, above all, sodium borohydride, or their derivatives in which one or more hydrogen atoms have been replaced by lower alkoxy radicals, such as methoxy-sodium borohydride and especially tri-tert.-butoxylithium aluminium hydride, are used for this purpose. The choice of the solvent and of the reducing conditions depends on the reducing agent used and conforms with the generally known principles. As has already been stated, however, it is also possible to carry out the conversion of the 17-oxo group into a 17-hydroxyl group with simultaneous introduction of an optionally substituted lower aliphatic hydrocarbon radical, for example one of those mentioned initially, by reacting a corresponding oxo compound with a corresponding organo-metallic compound in a manner which is in itself known. If the hydrocarbon radical to be introduced is a lower alkyl radical, a Grignard compound, for example a lower alkylmagnesium halide, such as methylmagnesium bromide or methylmagnesium iodide, or a lower alkyllithium, such as methyllithium, is preferred as the organo-metallic compound; when a 1-alkynyl radical, for example the 3-(2-tetrahydropyranyloxy)-propynyl, 3,3-ethylenedioxy-propynyl or 3-hydroxypropynyl radical, and especially the ethynyl radical, is to be introduced, a corresponding alkali metal compound, for example sodium acetylide or potassium acetylide or, in particular, lithium acetylide, is advantageously used. In the latter case it is particularly advantageous to use the lithium acetylide in the form of its complex with ethylenediamine. The ethynyl radical which is introduced can then be further converted by, for example, replacing the terminal hydrogen atom in this radical by a carboxyl group. This is effected by treatment with a Grignard compound and subsequent reaction of the resulting ω-magnesium halide with carbon dioxide. (The acetylenic 20(21)-bond can be saturated, as is described in more detail further below, directly after an acetylenic radical has been introduced or directly after the carboxylation.)- The introduction of a lower alkyl radical substituted by a disubstituted amino group, for example of a γ-di-lower alkylaminopropyl radical, especially one of those mentioned above as being preferred, is also carried out in an analogous manner; a suitable organo-metallic reagent to be mentioned is, above all, the corresponding γ-(di-lower alkylamino)propyllithium.

The optional saturation of the acetylenic bonds can be carried out, for example, in a manner which is in itself known, by catalytic hydrogenation. The triple bond can give a double bond in a first stage and this bond is optionally further saturated to a single bond. The catalytic hydrogenation is carried out using hydrogen gas under normal or elevated pressure under conditions of heterogeneous or homogeneous cataysis. Particularly suitable catalysts for heterogeneous catalysis are finely divided metals, for example Raney metals, such as Raney nickel, or noble metals, such as palladium, platinum or rhodium, which are optionally distributed on a support, such as calcium carbonate or barium sulphate. For homogeneous catalysis on the other hand, complex rhodium compounds, for example tris-(triphenylphosphine)-rhodium-I chloride, are used in particular. For the selective hydrogenation of a triple bond to a double bond, the Lindlar catalyst, viz. a palladium catalyst partially deactivated by lead, is advantageously used. The conditions for the hydrogenation are to be so chosen that the cyclopropane ring of the 6β,7-methylene grouping is not attacked.

The optional esterification or etherification of hydroxyl groups in resulting compounds is also carried out in a manner which is in itself known. For esterification, for example, the compound to be esterified is treated with an excess of the acid itself, such as with formic acid, or with a reactive derivative thereof, for example with a derivative of one of the acids indicated above, and in particular with an anhydride or acid halide, advantageously in the presence of a tertiary base, such as pyridine, quinoline or N-ethyl-piperidine. Hydroxyl groups which are different to esterify, such as, for exampe, a tertiary 17α-hydroxyl group, can advantageously be esterified with an acid anhydride under the catalytic influence of organic sulphonic acids, for example of benzenesulphonic acid, p-toluenesulphonic acid, sulphosalicyclic acid or camphorsulphonic acid. For etherification, for example, the compounds to be etherified are treated with reactive derivatives of alcohols, for example with esters with strong acids, such as halides, sulphates or sulphonic acid esters, the alcohol component corresponding to the meanings given above for an etherified hydroxyl group. Preferably, the reaction is carried out in the presence of basic agents. In order to form tetrahydropyranyl ethers and analogous 1-lower alkoxy-lower alkyl ethers, a corresponding unsaturated derivative, such as 2,3-dihydropyrane or a vinyl lower alkyl ether, for example vinyl butyl ether, is preferably used as the reagent and the reaction is carried out under the conditions of acid catalysis, preferably in the presence of an organic sulphonic acid. The silyl ethers, for example the hydroxy compounds etherified with tri-lower alkylsilyl groups, such as trimethylsilyl groups or dimethyl-tert.-butyl-silyl groups, can be manufactured by treatment with a corresponding silylating agent, such as trimethylchlorosilane, dimethyl-tert.-butyl-chlorosilane, hexamethyldisilazane, trimethylsilylamine, trimethylsilyl-diethylamine, dimethyl-tert.-butyl-silylimidazole, N-trimethylsilylacetamide or N,N-bis-(trimethylsilyl)-acetamide, in an anhydrous solvent, such as dimethylformamide, dimethyl sulphoxide or acetonitrile, and optionally in the presence of an anhydrous base, such as triethylamine, piperidine, pyridine or imidazole.

Unless it occurs spontaneously during the process stage (d), the optional closure of a lactone ring usually takes place spontaneously when a carboxyl group present as a salt is liberated by acidification. The formation of a lactone ring can also be accelerated by acid catalysis and/or the use of dehydrating agents, such as acetic anhydride, anhydrous copper sulphate or molecular sieves, or by azeotropic distillation.

Preferred starting materials for the process according to the invention are those compounds of the formula III in which $n$ represents the number 1, $R^2$ denotes a free hydroxyl group in the β-position and R has one of the following meanings: a free or ketalised oxo group; a β-oriented acetyl group (= α-oxoethyl group) together with a hydrogen atom; or a β-oriented etherified or esterified hydroxyl group together with hydrogen or a lower alkyl. Preferably, R denotes a substituent mentioned initially under the formula II, above all a substituent in which $R^1$ represents an oxo group, or also a corresponding open-chain form thereof, that is to say a free 17β-hydroxyl group together with an ethyl radical substituted in the β-position by hydroxymethyl, formyl or, in particular, carboxyl. As has already been stated above, the last-mentioned carboxyl group can also be in the form of a salt.

Preferred embodiments of the process according to the invention are those which lead to final products of the formula I in which R has the preferred meanings mentioned and among these embodiments, in particular those in which synthesis stages (a)–(d) follow immediately after one another. The use of the preferred starting materials ccntaining a free 3-hydroxy group also has the advantage that process stage (b) is then dispensed with.

A particularly preferred embodiment of the process according to the invention relates to the manufacture of 20-spirox-4-ene compounds of the formula

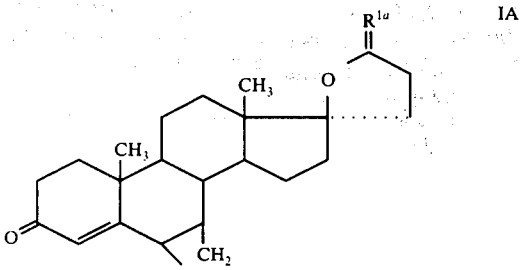

in which $R^{1a}$ denotes two hydrogen atoms or an oxo group, which is characterised in that the abovementioned process steps (a), (c) and (d) are carried out starting from a compound of the formula

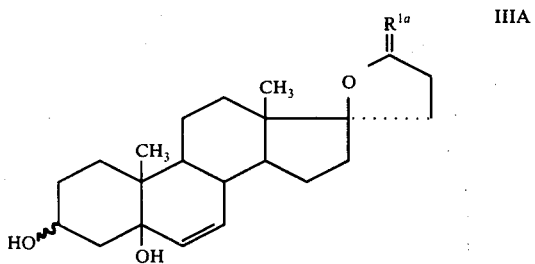

in which $R^{1a}$ has the indicated meaning.

As is known from the literature, compare German Offenlegungsschrift No. 1,914,507 and British Pat. Nos. 1,361,362 and 1,403,800, the compounds of the formula IA are highly active aldosterone inhibitors, both in the cyclic form which is shown and in the open-chain form of the corresponding hydroxyacid or of its alkali metal salts. They antagonise the salt-retention, which is caused by aldosterone and steroids of an analogous activity, and are therefore used for the alleviation of diseases in which the secretion of aldosterone is increased, such as in the case of cardiac insufficiency with congestive symptoms, nephrosis and cirrhosis of the kidneys.

The 6-en-3ξ,5β-diol steroids which are used as starting materials for the process according to the invention, and especially those of the formula III characterised above, are new and are also obtained according to a novel manufacturing process by treating a corresponding 3ξ-hydroxy-5β,6-epoxide, especially a 3ξ-hydroxy-5β,6-epoxide of the formula

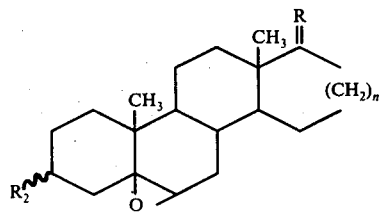

in which $n$, R and $R^2$ possess the meanings indicated above, successively with a selenol, a peroxidic oxidising agent and a base.

The selenol used is, in particular, a lower alkane- or arene-selenol, preferably a benzeneselenol (selenophenol) which is optionally substituted by lower alkyl, lower alkoxy or nitro groups and/or by halogen atoms, above all benzeneselenol. Because of its sensitivity to oxidation, the selenol used is preferably prepared in situ immediately prior to the reaction by reducing a corresponding symmetrical diselenide in a manner which is in itself known, for example with zinc and an acid, such as hydrochloric acid or acetic acid, or with a complex hydride, preferably sodium borohydride, with the exclusion of atmospheric oxygen. The addition of the selenol to the steroid giving rise to the corresponding 5β-hydroxy-6α-selenide is also carried out with the exclusion of atmospheric oxygen in an organic solvent, such as a lower alkanol or ether, for example one of those mentioned above, or in a mixture of several such solvents and is usually effected at an elevated temperature, advantageously in the range close to the boiling temperature of the reaction mixture.

The peroxidic oxidising agent is, in particular, an inorganic peroxyacid, such as, for example, mono- or di-peroxysulphuric acid, or an alkali metal salt thereof, or, in particular, an organic peroxyacid, such as peracetic acid, perbenzoic acid, m-chloroperbenzoic acid and monoperoxyphthalic acid, in the free form or in the form of corresponding alkali metal salts. However, hydrogen peroxide, preferably in the customary commercially available form of an approximately 30% strength aqueous solution, can also advantageously be used as the peroxidic oxidising agent. The oxidation, in which the 6α-selenide group (—Se—) is converted into the 6α-selenonyl group (—SeO$_2$—), takes place in a manner which is in itself known, preferably in a weakly acid or neutral medium with the use of organic solvents, preferably those which are miscible with water, for example the alcohols, ethers and polyethers mentioned above. The reaction temperature usually is between about $-25°$ and $+35°$.

Bases which are suitable for splitting off the 6α-selenonyl group in a 6α-selenonyl-3ξ,5β-diol, and especially in a 6α-phenylselenonyl-3ξ,5β-diol, with the formation of the desired 6,7-double bond in the steroid of the formula III, are, in particular, organic bases, such as tertiary amines, for example tri-lower alkylamines or aryl-di-lower alkylamines, especially phenyl-di-lower alkylamines, or heterocyclic bases, especially those which are at least partially saturated, for example N-ethylpiperidine, N-methylpyrrolidine or N,N'-dimethylpiperazine. A particularly advantageous base is 1,5-diazabicyclo[4.3.0]non-5-ene. The reaction can be carried out in an excess of the base as the solvent, or an inert organic solvent, preferably a water-miscible solvent, such as, for example, pyridine and its homologues, can be used. The reaction is usually carried out at elevated temperature, especially between about 45° and about 150° C., and, if desired, under elevated pressure. It is advantageous to allow the reaction to proceed with the exclusion of atmospheric carbon dioxide and oxygen and under anhydrous conditions.

The starting materials required for the conversion already described, i.e. 5β,6-epoxy-3ξ-hydroxy steroids, for example those of the formula IV, are known or are accessible by methods which are in themselves known, for example by addition of the elements of hypobromous acid onto the 5,6-double bond and subsequent elimination hydrogen bromide with a base.

The preferred compounds, substituents and meanings of the symbols are herein those which have been mentioned as preferred in the context of the formulae I to III.

The invention also relates to those embodiments of the above processes according to which a compound obtainable as an intermediate at any stage is used as the starting material and the missing steps are carried out, or according to which a starting material is formed under the reaction conditions.

The following Examples illustrate the invention in more detail, without restricting the scope thereof. The temperatures are given in degrees centigrade. The nomenclature used is derived from 20-spiroxane of the formula

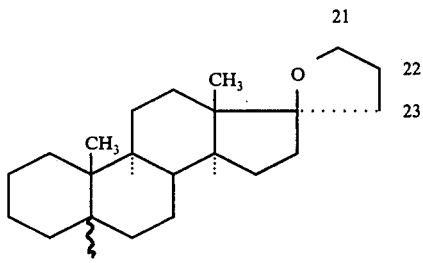

as the parent structure, the other fundamental principles of conventional steroid nomenclature being retained.

EXAMPLE 1

3.68 g of sodium borohydride are added in portions, in the course of 30 minutes, in a stream of nitrogen to a mixture of 14.4 g of diphenyl diselenide in 240 ml of absolute alcohol, while stirring and cooling with ice-water. After a further 30 minutes, the mixture is treated with 6 ml of glacial acetic acid, and 4.76 g of 5β,6-epoxy-3β-hydroxy-20-spiroxan-21-one acetate are then added. After boiling for 24 hours, the cooled reaction solution is poured into water, and the mixture is extracted several times with methylene chloride.

The organic phase is washed with a dilute solution of sodium chloride, dried and evaporated in vacuo, and the residue is dissolved in toluene and chromatographed on 200 g of silica gel. Initially, diphenyl diselenide is eluted with toluene. 3β,5β-Dihydroxy-6α-phenyl-seleno-20-spiroxan-21-one 3-acetate is then obtained by eluting with a mixture of toluene/ethyl acetate (7:3). After crystallisation from ether, the substance melts at 243°–247°.

The starting 5β,6-epoxy-3β-hydroxy-20-spiroxan-21-one acetate is obtained as follows:

(a) A stirred solution of 10g of 3β-hydroxy-20-spirox-5-en-21-one acetate in 100 ml of dioxane, is treated successively with 7.3 ml of dilute perchloric acid (prepared by diluting 4.66 ml of 70 percent strength perchloric acid with 20 ml of water), 5 ml of water and, in the course of 15 minutes with ice-cooling, with 5 g of N-bromoacetamide. After stirring for 30 minutes at room temperature, the reaction mixture is again cooled with ice-water, 60 ml of a 1 percent strength sodium thiosulphate solution and then water are added, and the mixture is extracted with ether. The organic extracts are washed with water, dried and evaporated in vacuo at room temperature. Crystallisation of the residue from ether gives 5α-bromo-3β,6β-dihydroxy-20-spiroxan-21-one 3-acetate with a melting point of 160°–162° (decomposition). Recrystallisation from acetone/methanol raises the melting point to 164°–165° (decomposition).

The starting material (5-en-3-ol acetate) is recovered by stirring the residue, which remains after evaporating the mother liquors, with zinc/copper alloy and glacial acetic acid.

(b) To a solution of 1.8 g of the bromohydrin acetate obtained under (a) in 25 ml of anhydrous dioxane, 900 mg of 1,5-diaza-bicyclo[4.3.0]non-5-ene are added in a stream of nitrogen and rinsed subsequently with 5 ml of dioxane. After 30 minutes the reaction mixture is treated with 2.25 ml of glacial acetic acid, poured into a saturated solution of sodium bicarbonate and extracted with toluene. The organic extracts are washed with water, dried and evaporated in vacuo. Chromatography of the residue on silica gel gives 5β,6-epoxy-3β-hydroxy-20-spiroxan-21-one acetate, melting point 187°–190°.

EXAMPLE 2

A mixture of 1.16 g of sodium acetate and 5 g of 3β,5β-dihydroxy-6α-phenyl seleno-20-spiroxan-21-one 3-acetate in 1.16 ml of glacial acetic acid, 94 ml of ethanol and 47 ml of tetrahydrofurane is treated dropwise, while stirring and cooling with ice, with 18.8 ml of 30 percent strength hydrogen peroxide in the course of 20 minutes, and the mixture is stirred for a further 2¼ hours at room temperature. The mixture is poured into a dilute sodium chloride solution, the product is taken up into methylene chloride. The organic solution is washed with dilute sodium chloride solution, dried and evaporated in vacuo. The residue is dissolved in 190 ml of pyridine, and the solution is warmed in a closed flask with 24 ml of 1,5-diaza-bicyclo[4.3.0]non-5-ene in a nitrogen atmosphere at 63° for 20 hours. 24 ml of glacial acetic acid are then added to the reaction mixture, while cooling with ice/methanol, the mixture is diluted with 1.5 l of water, and the product is taken up into toluene. The organic phase is washed successively with dilute sodium bicarbonate solution and with water, dried and evaporated in vacuo. The residue is filtered, as a solution in toluene, through 24 g of Florisil and the adsorbent is eluted with 1 liter of a mixture of toluene/ethyl acetate (4:1). The eluates are evaporated and the residue is crystallised from methylene chloride/ether. 3β,5β-Dihydroxy-20-spirox-6-en-21-one 3-acetate is obtained and after further crystallisation this melts at 185°–194°.

A solution of 2 g of the above 3-acetate in 200 ml of methanol is treated with 40 ml of 1 N sodium hydroxide solution under nitrogen. The mixture is left to stand for 6 hours, acidified with 78 ml of 1 N hydrochloric acid and after 6 minutes poured into 1.2 l of dilute sodium chloride solution. The product is taken up into methylene chloride by repeated extraction, the organic solutions are washed with dilute sodium chloride solution, dried and evaporated in vacuo. Crystallisation of the residue from methylene chloride/ether gives 3β,5β-dihydroxy-20-spirox-6-en-21-one with a melting point of 203°–204°.

EXAMPLE 3

To a mixture of 30 ml of ether, 4.32 g of methylene iodide and 1.62 g of zinc/copper alloy, 168 mg of iodine are added with stirring. As soon as decoloration has taken place within about one minute, a solution of 150 mg of 3β,5β-dihydroxy-20-spirox-6-en-21-one in 6.8 ml of 1,2-dimethoxyethane is added to the mixture and rinsed subsequently with 3.6 ml of ether, and the mixture is refluxed under a nitrogen stream for 17½ hours. The solids are filtered off with suction and rinsed successively with methylene chloride, water, methanol and methylene chloride. The filtrate is diluted with saturated ammonium chloride solution and extracted with methylene chloride. The organic phase is washed with dilute sodium chloride solution, dried and evaporated in vacuo. Purification of the residue by preparative thin-layer chromatography (silica gel; toluene/acetone/7:3) gives 3β,5β-dihydroxy-6β,7-methylene-20-spiroxan-21-one in the form of a pale yellow oil.

EXAMPLE 4

A mixture of 43 mg of 3β,5β-dihydroxy-6β,7-methylene-20-spiroxan-21-one and 50 mg of chromium trioxide in 3 ml of pyridine is stirred at room temperature for 16 hours, a solution of 200 mg of sodium sulphite in 4 ml of water is added and the mixture is diluted with an additional amount of water. The mixture is extracted with toluene, and 1.5 ml of glacial acetic acid are added to the toluene extract. The aqueous phase is treated with 2 ml of glacial acetic acid and extracted twice more with toluene. The organic extracts are combined, washed twice with water, dried and evaporated in vacuo. The residue is warmed with 3 ml of glacial acetic acid in a nitrogen atmosphere for one hour at 80°, and the volatile constituents are evaporated in vacuo. The residue is subjected to preparative thin layer chromatography (silica gel; toluene/acetone/4:1). 6β,7-Methylene-20-spirox-4-ene-3,21-dione, which is obtained as the main product, is recrystallised from ether; melting point 178.5°-179°.

What is claimed is:

1. Process for the manufacture of a 6 beta, 7-methylene-3-oxo-4-ene steroid of the general formula

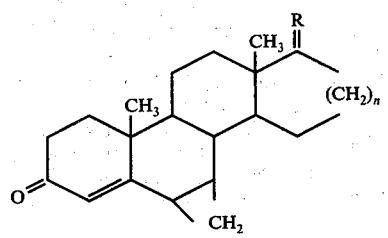

(I)

in which n denotes the number 1 to 2 and R represents a member selected from the group consisting of free oxo, ketalised oxo, free, etherified or esterified hydroxyl together with hydrogen, acetyl, hydroxyacetyl or a lower aliphatic hydrocarbon radical, beta-oriented hydroxyl together with y-di-lower alkylaminopropyl, hydrogen together with acetyl or hydroxyacetyl, and a radical, of the partical formula II

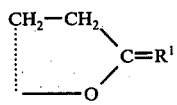

(II)

in which R¹ is two hydrogens, oxo, or lower alkoxy together with hydrogen, in which process, in consecutive steps, a compound of the formula III

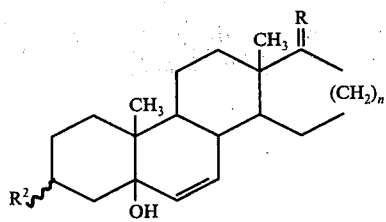

(III)

in which n and R have the abovementioned meanings and R² represents alpha-oriented or beta-oriented hydroxyl, such hydroxyl etherified by an easily detachable protective group, or such hydroxyl esterified by a carboxylic acid, (a) is reacted with a zinc/copper-methylene iodide reagent, (b) the 3-hydroxyl group in a 6beta,7-methylene-3ξ,5-diol, if present in an etherified or esterified form, is liberated by hydrolysis, (c) the resulting 6beta,7-methylene-3ξ,5beta-diol is treated with an oxidising agent in order to dehydrogenate the 3-hydroxyl group to a 3-oxo group and (d) the resulting 6beta,7-methylene-5beta-hydroxy-3-oxo compound is treated with a dehydrating agent in order to split off the 5beta-hydroxyl group with formation of a 4,5-double bond.

2. Process according to claim 1, wherein the symbol n in compounds of the formulae I and III represents the number 1.

3. Process according to claim 1, wherein a compound of the formula III, in which R² denotes a β-oriented free hydroxyl group, is reacted according to process stages (a), (c) and (d), stage (b) being omitted.

4. Process according to claim 1, wherein the symbol R in compounds of the formula I and III denotes a radical of the partial formula

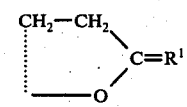

(II)

in which R¹ represents two hydrogen atoms, an oxo group, or a lower alkoxy group together with a hydrogen atom.

5. Process according to claim 1, wherein a 20-spirox-4-ene compound of the formula

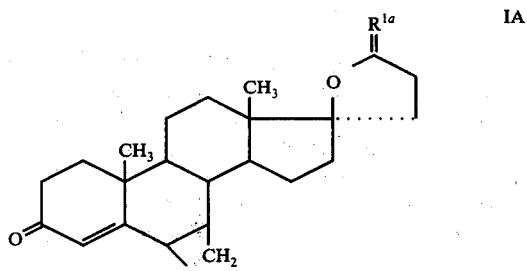

IA in which R¹ᵃ denotes two hydrogen atoms or an oxo group, is manufactured by reacting a compound of the formula

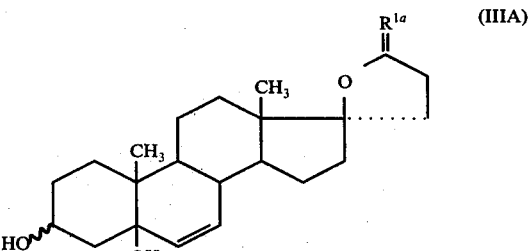

(IIIA)

in which R¹ᵃ has the meaning given successively with a zinc/copper-methylene iodide reagent in order to effect the addition of the 6β,7-methylene group, with an oxidising agent in order to effect dehydrogenation of the 3-hydroxyl group to an oxo group, and with a dehydrating agent in order to split off the 5β-hydroxyl group with the formation of a 4,5-double bond.

6. Process according to claim 5, wherein a compound of the formula IIIA in which the 3-hydroxyl group is 62-oriented is reacted.

7. Process according to claim 5, wherein chromium trioxide in pyridine is used as oxidising agent.

8. Process according to claim 5, wherein the oxidation product is heated in acetic acid in order to effect dehydration.

9. Process for the manufacture of a compound of the formula III

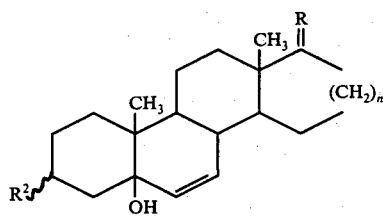

in which n denotes the number 1 or 2 and R represents a member selected from the group consisting of free oxo, ketalised oxo, free, etherified or esterified hydroxyl together with hydrogen, acetyl, hydroxyacetyl or a lower aliphatic hydrocarbon radical, beta-oriented hydroxyl together with gamma di-lower alkylaminopropyl, hydrogen together with acetyl or hydroxyacetyl, and a radical of the partial formula II

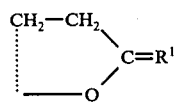

in which $R^1$ is two hydrogens, oxo, or lower alkoxy together with hydrogen, and $R^2$ represents alpha-oriented or beta-oriented hydroxyl, such hydroxyl etherified by an easily detachable protective group, or such hydroxyl esterified by a carboxylic acid, wherein a corresponding 3ξ-hydroxy-5beta, 6-epoxide of the formula IV

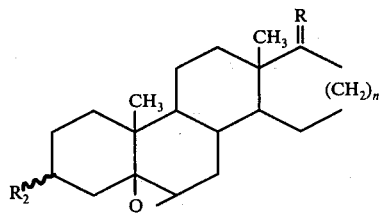

in which n, R and $R^2$ have the meaning indicated above, is treated successively (a) with a selenol selected from a lower alkaneselenol or areneselenol, (b) with a peroxidic oxidising agent selected from the group consisting of hydrogen peroxide, an anorganic peroxy acid and an organic peroxacid, and (c) with an organic base to split off the 6alpha-selenoyl with formation of the 6,7 double bond.

10. Process according to claim 9, wherein the symbol n in compounds of the formulae III and IV represents the number 1.

11. Process according to claim 9, wherein a compound of the formula

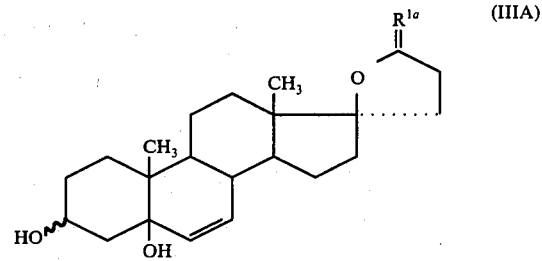

in which $R^{1a}$ denotes two hydrogen atoms or an oxo group is manufactured.

12. Process according to claim 9, wherein a compound of the formula III or IIIA is manufactured in which the hydroxyl group in the 3-position is β-oriented.

13. Process according to claim 9, wherein compound of the formula IV is treated with benzeneselenol.

14. Process according to claim 9, wherein the oxidising agent is aqueous hydrogen peroxide of approximately 30% strength.

15. Process according to claim 9, wherein the organic base is 1,5-diazabicyclo[4.3.0]non-5-ene.

16. Process according to claim 9, wherein a 3-hydroxyl group present in an esterified form in the starting material is liberated by base hydrolysis following the stage (c).

17. A compound of, the formula IIIA

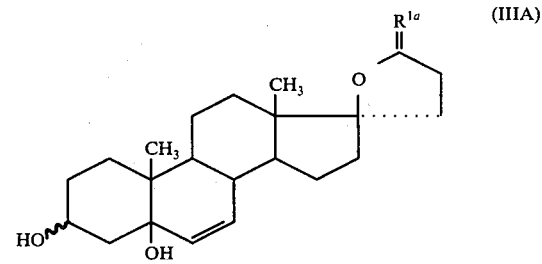

in which $R^{1a}$ denotes two hydrogen atoms or an oxo group; or a lower alkanoate thereof.

18. A compound according to claim 17, wherein the substituent in the 3-position is β-oriented.

19. A compound according to claim 17, which compound is the 3beta,5beta-dihydroxy-20-spirox-6-en-21-one 3acetate.

20. A compound according to claim 17, which compound is the 3beta,5beta-dihydroxy-20-spirox-6-en-21-one.

* * * * *